United States Patent
Kato et al.

(10) Patent No.: US 12,156,926 B2
(45) Date of Patent: Dec. 3, 2024

(54) TOPICAL COMPOSITION FOR NANOBUBBLE COSMETIC

(71) Applicant: TOA Inc., Osaka (JP)

(72) Inventors: Hideki Kato, Kashiwara (JP); Takeo Yoneda, Kashiwara (JP); Seiki Hori, Kashiwara (JP); Hideki Nishiura, Osaka (JP); Takahito Nakai, Osaka (JP)

(73) Assignee: TOA Inc., Osaka (JP)

( * ) Notice: Subject to any disclaimer, the term of this patent is extended or adjusted under 35 U.S.C. 154(b) by 0 days.

(21) Appl. No.: 18/029,864

(22) PCT Filed: Nov. 5, 2021

(86) PCT No.: PCT/JP2021/040809
§ 371 (c)(1),
(2) Date: Mar. 31, 2023

(87) PCT Pub. No.: WO2022/010000
PCT Pub. Date: Jan. 13, 2022

(65) Prior Publication Data
US 2023/0293394 A1 Sep. 21, 2023

(30) Foreign Application Priority Data
Sep. 7, 2021 (JP) .................. 2021-145577

(51) Int. Cl.
| | | |
|---|---|---|
| A61K 8/02 | (2006.01) | |
| A61K 8/04 | (2006.01) | |
| A61K 8/34 | (2006.01) | |
| A61K 8/35 | (2006.01) | |
| A61K 8/37 | (2006.01) | |
| A61K 8/49 | (2006.01) | |
| A61K 8/55 | (2006.01) | |
| A61K 8/63 | (2006.01) | |
| A61Q 1/14 | (2006.01) | |
| A61Q 11/00 | (2006.01) | |
| A61Q 19/10 | (2006.01) | |

(52) U.S. Cl.
CPC ............ *A61K 8/0291* (2013.01); *A61K 8/046* (2013.01); *A61K 8/34* (2013.01); *A61K 8/345* (2013.01); *A61K 8/35* (2013.01); *A61K 8/37* (2013.01); *A61K 8/4973* (2013.01); *A61K 8/553* (2013.01); *A61K 8/63* (2013.01); *A61Q 1/14* (2013.01); *A61Q 11/00* (2013.01); *A61Q 19/10* (2013.01)

(58) Field of Classification Search
CPC .......... A61K 2800/10; A61K 2800/222; A61K 2800/413; A61K 2800/54; A61K 2800/59; A61Q 90/00
USPC .............................................. 424/401, 78.03
See application file for complete search history.

(56) References Cited

U.S. PATENT DOCUMENTS

| | | |
|---|---|---|
| 2017/0189943 A1 | 7/2017 | Murata et al. |
| 2019/0254938 A1* | 8/2019 | Hayakawa ........... A61K 8/8176 |
| 2022/0387469 A1 | 12/2022 | Kinoshita et al. |

FOREIGN PATENT DOCUMENTS

| | | | |
|---|---|---|---|
| CN | 104434585 A | 3/2015 | |
| CN | 112675065 A | 4/2021 | |
| CN | 112843185 A | 5/2021 | |
| JP | 2008127342 A | 6/2008 | |
| JP | 2013014540 | * 1/2013 | ............... A61K 8/44 |
| JP | 2016132626 A | 7/2016 | |
| JP | 2019131492 A | 8/2019 | |
| JP | 2020037542 A | 3/2020 | |
| JP | 2020147520 A | 9/2020 | |
| JP | D1678824 S | 2/2021 | |
| JP | 2021030171 A | 3/2021 | |
| JP | D1681286 S | 3/2021 | |
| JP | D1689485 S | 7/2021 | |
| JP | D1689486 S | 7/2021 | |
| KR | 1020190122044 A | 10/2019 | |
| WO | 2015182647 A1 | 12/2015 | |
| WO | 2021085628 A1 | 5/2021 | |
| WO | 2021085633 A1 | 5/2021 | |
| WO | 2021144889 A1 | 7/2021 | |

OTHER PUBLICATIONS

Office Action of the Japanese Patent Office in related Japanese Patent Appl. 2021-568540, dated May 31, 2022, 6 pages.
Office Action of the Japanese Patent Office in related Japanese Patent Appl. 2021-568540, dated Aug. 30, 2022, 8 pages.
Beauty Serum, Unilife Japan, May 2017, Mintel GNPD, Accession No. 4807861 in particular, product description, content of the appeal, component, retrieved from https://www.gnpd.com.
International Search Report and Written Opinion dated Jan. 11, 2022, in related International Appl. No. PCT/JP2021/040809, 10 pages.
Mintel GNPD (mintel.com), "Luxury Fragrant Body Wash", Shantou Runjing Cosmetics, Jun. 2020, 2 pages.
Examination Report of the United Kingdom Patent Office in related UK Patent Appl. No. GB2304859.8, dated May 17, 2023, 6 pages.

(Continued)

*Primary Examiner* — Walter E Webb
(74) *Attorney, Agent, or Firm* — Bochner PLLC; Andrew Bochner; Eric Kleinertz

(57) ABSTRACT

The present invention provides a topical composition for a nanobubble cosmetic with which functional properties required by various types of cosmetic products can be improved. The present invention is a topical composition for a nanobubble cosmetic to be used in a container equipped with a device mechanism for generating nanobubbles, the topical composition containing a polyoxypropylene diglyceryl ether and ethoxydiglycol, or containing hyaluronic acid or a salt thereof, or containing ethanol and menthol or a derivative thereof, or containing sorbitol and glycerin, or containing phytosteryl/octyldodecyl lauroyl glutamate, or containing glycereth-26, or containing hydrogenated lecithin and polysorbate 20, or containing ethanol and polysorbate 20.

1 Claim, No Drawings

(56) References Cited

OTHER PUBLICATIONS

First Office Action of the China National Intellectual Property Administration (CNIPA) dated Sep. 6, 2023, in related Chinese Patent Appl. No. 202180066545.0, 11 pages.

* cited by examiner

TOPICAL COMPOSITION FOR NANOBUBBLE COSMETIC

TECHNICAL FIELD

The present invention relates to a topical composition for a nanobubble cosmetic to be used in a container equipped with a device mechanism for generating nanobubbles.

BACKGROUND ART

In general, attempts have been made to improve the functionality of liquids, such as the cleaning effect of liquids and the functional improvement of foods, by generating ultrafine bubbles, so-called nanobubbles, in a liquid. For the generation of nanobubbles, a method using chemicals, a pressurized dissolution method, a liquid two-phase swirl method, in which water and gas are stirred, and the like are known.

Conventionally, there is known a container equipped with a device mechanism for generating nanobubbles, which is provided with a device for generating nanobubbles, as a container for holding a topical composition for a cosmetic such as a lotion. For example, as a container equipped with a device mechanism for generating nanobubbles, the container equipped with a device mechanism for generating nanobubbles of Patent Document 1 and parts for nanobubble generation of Patent Documents 2 to 5 are known. The container equipped with a device mechanism for generating nanobubbles of Patent Document 1 is composed of a container body and a pump unit detachably inserted into the container body. The liquid in the container body passes through the narrow gap of a check valve for preventing air inflow in the pump unit or the narrow gap between a piston and a piston guide, and is discharged from the discharge port. The gap provided in the middle of the passage that communicates with the discharge port causes the liquid to undergo a shear crushing action to generate nanobubbles. Patent Documents 2 to 5 disclose disc-shaped plates provided with small holes or stirring balls of ultra-fine mesh. The parts of Patent Documents 2 to 4 are arranged in a container. When this container is filled with a liquid such as a cosmetic liquid and is vibrated or shaken, nanobubbles are generated by the liquid passing through small holes provided in the disc-shaped plate. The part of Patent Document 5 is arranged in a container. When this container is filled with a liquid such as a cosmetic liquid and is vibrated or shaken, the liquid comes into contact with the stirring balls of ultrafine mesh to generate nanobubbles in the solution.

CITATION LIST

Patent Literature

Patent Document 1: Japanese Laid-Open Patent Publication No. 2021-30171

Patent Document 2: Japanese Registered Design No. 1689485

Patent Document 3: Japanese Registered Design No. 1689486

Patent Document 4: Japanese Registered Design No. 1681286

Patent Document 5: Japanese Registered Design No. 1678824

SUMMARY OF INVENTION

Technical Problem

Improvement in functionality required for a wide variety of cosmetics has been demanded.

Solution to Problem

As a result of research to solve the above problem, the inventors of the present application have found that, in a topical composition for a nanobubble cosmetic to be used in a container equipped with a device mechanism for generating nanobubbles, using a specific key material further improves the cosmetic functionality.

In order to solve the above problem and in accordance with one aspect of the present invention, a topical composition for a nanobubble cosmetic is used in a container equipped with a device mechanism for generating nanobubbles and contains polyoxypropylene diglyceryl ether and ethoxydiglycol, hyaluronic acid or a salt thereof, ethanol and menthol or a derivative thereof, sorbitol and glycerin, di(phytosteryl/octyldodecyl)lauroyl glutamate, glycereth-26, hydrogenated lecithin and polysorbate 20, or ethanol and polysorbate 20.

The topical composition for a nanobubble cosmetic may contain polyoxypropylene diglyceryl ether and ethoxydiglycol and be used as a cleansing agent.

The topical composition for a nanobubble cosmetic may contain hyaluronic acid or a salt thereof and be used as a beauty essence or lotion.

The topical composition for a nanobubble cosmetic may contain ethanol and menthol or a derivative thereof and be used as a mouthwash.

The topical composition for a nanobubble cosmetic may contain sorbitol and glycerin and be used as a foamy cleaning composition.

The topical composition for a nanobubble cosmetic may contain di(phytosteryl/octyldodecyl) lauroyl glutamate and be used as a facial cleansing composition.

The topical composition for a nanobubble cosmetic may contain glycereth-26 and be used as a lotion.

The topical composition for a nanobubble cosmetic may contain hydrogenated lecithin and polysorbate 20 and be used as an emulsion.

The topical composition for a nanobubble cosmetic may contain ethanol and menthol or a derivative thereof and be used as a deodorant cosmetic.

The topical composition for a nanobubble cosmetic may contain ethanol and polysorbate 20 and be used as a perfuming cosmetic.

Advantageous Effects of Invention

The present invention succeeds in further improving the functionality required for a wide variety of cosmetics.

DESCRIPTION OF EMBODIMENTS

Hereinafter, a topical composition for a nanobubble cosmetic according to one embodiment of the present invention will be described. The topical composition for a nanobubble cosmetic of the present embodiment contains, as an active ingredient, one of the following: polyoxypropylene diglyceryl ether and ethoxydiglycol; hyaluronic acid or a salt thereof; ethanol and menthol or a derivative thereof; sorbitol and glycerin; di(phytosteryl/octyldodecyl) lauroyl glutamate; glycereth-26; hydrogenated lecithin and polysorbate 20; and ethanol and polysorbate 20. The topical composition for a nanobubble cosmetic is used in a container equipped with a device mechanism for generating nanobubbles to further improve the functionality required for a wide variety of cosmetics.

The term "functionality" in the present invention is not limited to necessary and essential functions such as detergency in cleansing agents, and includes the functionality based on the product concept of the implementation of the invention, such as optional functions including foaming, foam breaking, and foam persistence in cleansing agents. Furthermore, for example, common technical features regardless of product category such as formulation safety (for example, reduction, prevention, or substitution of discomfort and irritation during use, improvement of biocompatibility) and stability (for example, reduction or prevention of discoloration or separation) are included.

Active Component

Examples of active components include a combination of polyoxypropylene diglyceryl ether and ethoxydiglycol, hyaluronic acid or a salt thereof, a combination of ethanol and menthol or a derivative thereof, a combination of sorbitol and glycerin, di(phytosteryl/octyldodecyl) lauroyl glutamate, glycereth-26, a combination of hydrogenated lecithin and polysorbate 20, and a combination of ethanol and polysorbate 20. Specific examples of polyoxypropylene diglyceryl ether include PPG-9 diglyceryl ether. Specific examples of hyaluronic acid salts include: alkali metal salts, such as sodium salts and potassium salts; alkaline earth metal salts, such as magnesium salts and calcium salts; zinc salts; and ammonium salts. Specific examples of menthol or a derivative thereof include 1-menthol, dl-menthol, menthoxypropanediol, monomenthyl glyceryl ether, menthyl lactate, menthyl acetate, menthone, and menthanediol. Peppermint oil, Mentha piperita oil, spearmint oil, and the like, containing menthol, may be used as menthol. In a case of using a combination of sorbitol and glycerin, it is preferable to apply foam as the dosage form.

Container Equipped with Device Mechanism for Generating Nanobubbles

An applicable container equipped with a device mechanism for generating nanobubbles includes a known device equipped with a container capable of holding or being filled with the topical composition for a cosmetic described above. The diameter of the nanobubbles is several hundred nanometers to 10 μm or less, and microbubbles shrink in water to change to nanobubbles. The dosage form of the composition discharged from the container is not particularly limited, and examples thereof include a spray type, a mist type, a liquid discharge type, a foam type, and a type of directly discharging or taking out the composition from an opening. Examples of the device include a container equipped with a device mechanism for generating nanobubbles, in which a gap for generating nanobubbles by causing a shear crushing action on a liquid is provided in the middle of the passage communicating with a discharge port. More specific examples thereof include a device including: a piston reciprocally built in a discharging device; a piston guide that regulates the reciprocation of the piston; a discharge port provided on the discharge side of the device; and a check valve provided on the bottle side of the device. Nanobubbles are generated by causing shear crushing to a liquid while the liquid is delivered through the gap between the piston and the piston guide to the discharge port. In such a device, the gap between the piston and the piston guide is preferably 0.2 mm or less.

Examples thereof also include a container equipped with one or more disc-shaped plates with small holes. The disc-shaped plate is arranged so as to be substantially perpendicular to the shaking direction. When this container is filled with or holds a liquid such as a cosmetic liquid and is vibrated or shaken, nanobubbles are generated by the liquid passing through small holes provided in the disc-shaped plate. Examples thereof also include a container equipped with stirring balls of ultra-fine mesh in the container. When this container is filled with or holds a liquid such as a cosmetic liquid and is vibrated or shaken, nanobubbles are generated in the solution by the liquid coming into contact with the stirring balls of ultrafine mesh.

Examples thereof also include a container holding nanobubble-generating stirring balls, the container being a hollow body having a hollow structure and having holes in the wall surface of the hollow structure through which a liquid will pass. Nanobubbles are generated by shear crushing action when a liquid such as a cosmetic liquid is filled or held in a container holding nanobubble-generating stirring balls and is vibrated or shaken.

Topical Composition for Cosmetic

The topical composition for a cosmetic is not particularly limited, and examples thereof include: a skin cosmetic compositions, such as a cleansing agent, beauty essence, facial cleanser, lotion, emulsion, pack cosmetic, body soap, body care, deodorant cosmetic, perfuming cosmetic (fragrance), anti-wrinkle cosmetic, acne care cosmetic, hand care cosmetic, sunscreen, foundation, nail polish, or nail polish remover; a quasi-drug, such as an acne care agent or hand sanitizer; a cosmetic composition for the scalp or hair, such as a shampoo, rinse, treatment, conditioner, hair restorer, hair dye, bleaching agent, or hair styling agent; and an oral composition, such as a mouth wash or mouth spray. The dosage form of the topical composition for a cosmetic includes foam, liquid, and emulsion.

Each composition contains a base material composed of known components in addition to the active components described above. Hereinafter, cleansing agents, beauty essences, mouthwashes, facial cleansing compositions, lotions, emulsions, deodorant cosmetics, perfuming cosmetics, and foamy cleaning compositions will be described in more detail.

Cleansing Agent

The cleansing agent contains polyoxypropylene diglyceryl ether and ethoxydiglycol as active components in addition to the base material. Application of the cleansing agent as a nanobubble cosmetic containing polyoxypropylene diglyceryl ether and ethoxydiglycol as active ingredients further improves the detergency and makeup removing effect in particular.

The lower limit of the content of polyoxypropylene diglyceryl ether in the cleansing agent is preferably 1% by mass or more, more preferably 5% by mass or more. When the content is 1% by mass or more, the detergency and makeup removing effect are further improved. The upper limit of the content of polyoxypropylene diglyceryl ether is preferably 20% by mass or less, more preferably 15% by mass or less. When the content is 20% by mass or less, the detergency and makeup removing effect are improved more efficiently. Ranges with any combination of the above upper and lower limits are also available for use.

The lower limit of the content of ethoxydiglycol in the cleansing agent is preferably 0.5% by mass or more, more preferably 1% by mass or more. When the content is 0.5% by mass or more, the detergency and makeup removing effect are further improved. The upper limit of the content of ethoxydiglycol is preferably 5% by mass or less, more preferably 4% by mass or less. When the content is 5% by mass or less, the detergency and makeup removing effect are improved more efficiently. Ranges with any combination of the above upper and lower limits are also available for use.

Examples of the base material include water, solvents, polyhydric alcohols, oily components, surfactants, pH adjusters, chelating agents, preservatives, fragrances, antioxidants, thickeners, sugars, moisturizers, and other known additives.

Specific examples of the solvents include ethanol, n-propanol, isopropanol, methyl cellosolve, ethyl cellosolve, methyl carbitol, ethyl carbitol, benzyl alcohol, phenethyl alcohol, γ-phenylpropyl alcohol, cinnamic alcohol, anis alcohol, p-methylbenzyl alcohol, α-dimethylphenethyl alcohol, α-phenylethanol, ethylene glycol phenyl ether (phenoxyethanol), phenoxyisopropanol, 2-b enzyloxyethanol, N-alkylpyrrolidone, alkylene carbonate, and alkyl ether. These solvents may be contained singly or in a combination of two or more.

Examples of the oily components include oils and fats, waxes, hydrocarbons, higher fatty acids, alkylglyceryl ethers, esters, and silicones. These oily components may be contained singly or in a combination of two or more. Specific examples of the oily components include squalane, lauric acid, myristic acid, and palmitic acid.

Examples of the polyhydric alcohols include glycol and glycerin. Specific examples of glycol include ethylene glycol, diethylene glycol, triethylene glycol, polyethylene glycol, high polymer polyethylene glycol, propylene glycol, dipropylene glycol, polypropylene glycol, isoprene glycol, 1,3-butylene glycol, pentylene glycol, and 1,2-hexanediol. Specific examples of glycerin include glycerin, diglycerin, and polyglycerin. These polyhydric alcohols may be contained singly or in a combination of two or more.

Examples of the surfactant include nonionic surfactants, anionic surfactants, cationic surfactants, and amphoteric surfactants.

Examples of the cationic surfactant include quaternary ammonium salts, ether-type quaternary ammonium salts, tertiary amines, and pyridinium-based surfactants.

Examples of the anionic surfactant include alkyl ether sulfates, alkyl sulfates, alkyl ether sulfates, alkenyl ether sulfates, alkenyl sulfates, olefinsulfonates, alkanesulfonates, saturated or unsaturated fatty acid salts, alkyl or alkenyl ether carboxylates, α-sulfone fatty acid salts, N-acyl amino acid type surfactants, phosphoric acid mono- or diester surfactants, sulfosuccinic acid esters, N-acyl taurine salts, and derivatives thereof. Specific examples of counter ions for the anionic groups of these surfactants include sodium ions, potassium ions, and triethanolamine.

Examples of the nonionic surfactant include POE alkyl ethers, POE alkylphenyl ethers, POE/POP alkyl ethers, POE sorbitan fatty acid esters, POE mono fatty acid esters, POE glycerin fatty acid esters, sorbitan fatty acid esters, sucrose fatty acid esters, alkyl polyglucosides, alkyl glucosides, and fatty acid alkanolamides.

Examples of the amphoteric surfactant include amino acid type amphoteric surfactants, betaine type amphoteric surfactants, and sulfobetaine type amphoteric surfactants.

These surfactants may be contained singly or in a combination of two or more.

Specific examples of the chelating agent include ethylenediaminetetraacetic acid (EDTA, edetic acid), hydroxyethyl ethylenediaminetriacetic acid (HEDTA), dihydroxyethylethylenediaminediacetic acid (DHEDDA), 1,3-propanediaminetetraacetic acid (1,3PDTA), diethylenetriaminepentaacetic acid (DTPA, pentetic acid), triethylenetetraminehexaacetic acid (TTHA), nitrilotriacetic acid (NTA), hydroxyethyliminodiacetic acid (HIMDA), L-aspartic acid-N,N-diacetic acid (ASDA), salts thereof, derivatives thereof, and salts of derivatives thereof. Examples of the salt include alkali metal salts, such as sodium salts and potassium salts. These chelating agents may be contained singly or in a combination of two or more.

Specific examples of the thickener include sodium polyacrylate, carrageenan, sodium carboxymethylcellulose, sodium alginate, xanthan gum, hydroxyethyl cellulose, hydroxypropyl methylcellulose, methylcellulose, propylene glycol alginate, carbomer, and (acrylates/C10-30 alkyl acrylate) crosspolymer. These thickeners may be contained singly or in a combination of two or more.

Specific examples of the sugar include sucrose, trehalose, maltose, glycosyltrehalose, sorbitol, xylitol, maltitol, and N-acetylglucosamine. These sugars may be contained singly or in a combination of two or more. Specific examples of the moisturizer include glycerin, sorbitol, glycereth-26, butylene glycol (BG), propylene glycol (PG), dipropylene glycol (DPG), pentylene glycol, PEG-32, ethylhexylglycerin, and PEG/PPG/polybutylene glycol-8/5/3 glycerin. These moisturizers may be contained singly or in a combination of two or more.

Specific examples of the preservative include methylparaben, ethylparaben, propylparaben, phenoxyethanol, sodium benzoate, potassium sorbate, and dehydroacetic acid.

Examples of the pH adjuster include inorganic acids, organic acids, salts thereof, and alkali agents. Specific examples of the inorganic acid include phosphoric acid, hydrochloric acid, nitric acid, sulfuric acid, boric acid, and carbonates. Specific examples of the organic acid include citric acid, tartaric acid, lactic acid, malic acid, succinic acid, fumaric acid, maleic acid, pyrophosphate, gluconic acid, glucuronic acid, and benzoic acid. Specific examples of the organic acid salt include sodium salts, potassium salts, and ammonium salts. Examples of the alkaline agent include sodium hydroxide, potassium hydroxide, ammonia, and alkanolamine. These pH adjusters may be contained singly or in a combination of two or more.

Beauty Essence

The beauty essence contains hyaluronic acid or a salt thereof as an active component in addition to the base material. Hyaluronic acid or a salt thereof is blended for imparting moisturizing properties. Application of the beauty essence as a nanobubble cosmetic containing hyaluronic acid or a salt thereof as an active component improves penetrating properties and improves feeling of use such as penetrating feel, refreshing feeling, and firmness.

The lower limit of the content of hyaluronic acid or a salt thereof in the beauty essence is preferably 0.01% by mass or more, more preferably 0.05% by mass or more. When the content is 0.01% by mass or more, the moisturizing properties can be further improved. The upper limit of the content of hyaluronic acid or a salt thereof is preferably 2% by mass or less, more preferably 1% by mass or less. When the content is 2% by mass or less, the moisturizing properties can be improved more efficiently. In addition, stickiness is further suppressed. Ranges with any combination of the above upper and lower limits are also available for use.

Examples of the base material include water, solvents, polyhydric alcohols, oily components, surfactants, pH adjusters, chelating agents, preservatives, fragrances, antioxidants, beauty components, thickeners, sugars, moisturizers, and other known additives. As the beauty components, known components can be appropriately used depending on the purpose of the cosmetic, such as prevention of spots and wrinkles, improvement of firmness, moisturizing, and whitening. As specific examples of each component exemplified as the base material, those described above can be appropriately adopted.

A cosmetic containing hyaluronic acid or a salt thereof as an active component may be applied as a lotion. Application of the lotion as a nanobubble cosmetic containing hyaluronic acid or a salt thereof as an active component improves penetrating properties and improves feeling of use such as penetrating feel, refreshing feeling, and firmness.

Lotion

The lotion contains glycereth-26 as an active component in addition to the base material. Glycereth-26 is blended to impart moisturizing properties. Application of the lotion as a nanobubble cosmetic containing glycereth-26 as an active component improves penetrating properties and improves feeling of use such as penetrating feel, refreshing feeling, and firmness.

The lower limit of the content of glycereth-26 in the lotion is preferably 0.1% by mass or more, more preferably 0.5% by mass or more. When the content is 0.1% by mass or more, the moisturizing properties are further improved. The upper limit of the content of glycereth-26 is preferably 5% by mass or less, more preferably 2% by mass or less. When the content is 5% by mass or less, the moisturizing properties are improved more efficiently. In addition, stickiness is further suppressed. Ranges with any combination of the above upper and lower limits are also available for use.

Examples of the base material include water, solvents, polyhydric alcohols, oily components, surfactants, pH adjusters, chelating agents, preservatives, fragrances, antioxidants, beauty components, thickeners, sugars, moisturizers, and other known additives. As the beauty components, known components can be appropriately used depending on the purpose of the cosmetic, such as prevention of spots and wrinkles, improvement of firmness, moisturizing, and whitening. As specific examples of each component exemplified as the base material, those described above can be appropriately adopted.

Mouthwash

The mouthwash contains ethanol and menthol or a derivative thereof as active components in addition to the base material. Ethanol is blended for sterilization or detergency improvement. Application of the mouthwash as a nanobubble cosmetic containing ethanol and menthol or a derivative thereof as active components improves the effects of preventing bad breath and removing dental plaque while reducing alcohol-derived discomfort. In addition, the stickiness during use is reduced, and the sustainability of the refreshing feeling is improved.

The lower limit of the content of ethanol in the mouthwash is preferably 1% by mass or more, more preferably 5% by mass or more. When the content is 1% by mass or more, the sterilization or detergency is further improved. The upper limit of the ethanol content is not particularly limited, and it is, for example, 20% by mass or less. When the content is 20% by mass or less, discomfort is further reduced. Ranges with any combination of the above upper and lower limits are also available for use.

The lower limit of the content of menthol or a derivative thereof in the mouthwash is preferably 0.005% by mass or more, more preferably 0.01% by mass or more, and still more preferably 0.02% by mass or more. When the content is 0.005% by mass or more, the refreshing feeling is further improved. The upper limit of the content of menthol or a derivative thereof is preferably 1% by mass or less, more preferably 0.5% by mass or less. When the content is 1% by mass or less, the refreshing feeling is improved more efficiently. Ranges with any combination of the above upper and lower limits are also available for use.

Examples of the base material include water, antibacterial agents, anti-inflammatory agents, wetting agents such as polyhydric alcohols, surfactants, sweeteners, medicinal ingredients, pH adjusters, chelating agents, preservatives, fragrances, antioxidants, thickeners, and other known additives.

Specific examples of the antibacterial agent include cetylpyridinium chloride, paraben, sodium benzoate, triclosan, chlorhexidine hydrochloride, isopropylmethylphenol (o-cymen-5-ol), benzalkonium chloride, and benzethonium chloride. Specific examples of the anti-inflammatory agent include glycyrrhizinate, tranexamic acid, ε-aminocaproic acid, and phellodendron extract. Specific examples of the sweetener include sorbitol, saccharin, sodium saccharin, sucralose, stevioside, acesulfame cam, aspartame, xylitol, maltitol, and erythritol.

As specific examples of the other components, those applicable as a mouthwash from among the specific examples described above can be appropriately used.

Facial Cleansing Composition

The facial cleansing composition contains di(phytosteryl/octyldodecyl) lauroyl glutamate as an active component in addition to the base material. Di(phytosteryl/octyldodecyl) lauroyl glutamate is an oily amino acid ester and is blended to improve detergency while improving the feeling of use after washing the face. Application of the facial cleansing composition as a nanobubble cosmetic containing di(phytosteryl/octyldodecyl) lauroyl glutamate as an active component improves the detergency while improving the feeling of use by suppressing the feeling of tightness after washing.

The lower limit of the content of di(phytosteryl/octyldodecyl) lauroyl glutamate in the facial cleansing composition is preferably 0.01% by mass or more, more preferably 0.02% by mass or more. When the content is 0.01% by mass or more, the feeling of use and detergency are further improved. The upper limit of the content of di(phytosteryl/octyldodecyl) lauroyl glutamate is preferably 2% by mass or more, more preferably 1% by mass or more. When the content is 2% by mass or less, the feeling of use and detergency are improved more efficiently. Ranges with any combination of the above upper and lower limits are also available for use.

Examples of the base material include water, solvents, polyhydric alcohols, oily components, surfactants, pH adjusters, chelating agents, preservatives, fragrances, antioxidants, thickeners, sugars, moisturizers, beauty components, and other known additives. As specific examples of each component exemplified as the base material, those described above can be appropriately used.

Emulsion

The emulsion contains hydrogenated lecithin and polysorbate 20 as active components in addition to the base material. Hydrogenated lecithin is blended as an emulsifier and moisturizer. It also improves emulsion stability. Polysorbate 20 is an ethylene oxide condensation type polyoxyethylene sorbitan fatty acid ester as a nonionic surfactant, and improves the stability of emulsion. Application of the emulsion as a nanobubble cosmetic containing hydrogenated lecithin and polysorbate 20 as active components improves the penetrating properties and improves the feeling of use such as penetrating feel.

The lower limit of the content of hydrogenated lecithin in the emulsion is preferably 0.1% by mass or more, more preferably 0.5% by mass or more. When the content is 0.1% by mass or more, the moisturizing properties and stability of the emulsion are further improved. The upper limit of the content of hydrogenated lecithin is preferably 5% by mass or less, more preferably 2% by mass or less. When the content is 5% by mass or less, the moisturizing properties and stability of the emulsion are improved more efficiently. Ranges with any combination of the above upper and lower limits are also available for use.

The lower limit of the content of polysorbate 20 in the emulsion is preferably 0.01% by mass or more, more preferably 0.05% by mass or more. When the content is 0.01% by mass or more, the moisturizing properties are further improved. The upper limit of the content of polysorbate 20 is preferably 2% by mass or less, more preferably 1% by mass or less. When the content is 2% by mass or less, the penetrating properties are improved more efficiently. Ranges with any combination of the above upper and lower limits are also available for use.

Examples of the base material include water, solvents, polyhydric alcohols, oily components, surfactants, pH adjusters, chelating agents, preservatives, fragrances, antioxidants, thickeners, sugars, moisturizers, beauty components, and other known additives. As specific examples of each component exemplified as the base material, those described above can be appropriately used.

Foamy Cleaning Composition

The foamy cleaning composition contains sorbitol and glycerin as active components in addition to the base material. Application of the foamy cleaning composition as a nanobubble cosmetic containing sorbitol and glycerin as active components improves the foam quality.

The lower limit of the content of sorbitol in the foamy cleaning composition is preferably 0.5% by mass or more, more preferably 1% by mass or more. When the content is 0.5% by mass or more, foaming and foam quality are further improved. The upper limit of the content of the foamy cleaning composition is preferably 10% by mass or less, more preferably 5% by mass or less. When the content is 10% by mass or less, foaming and foam quality are improved more efficiently. Ranges with any combination of the above upper and lower limits are also available for use.

The lower limit of the content of glycerin in the foamy cleaning composition is preferably 1% by mass or more, more preferably 2% by mass or more. When the content is 1% by mass or more, foaming and foam quality are further improved. The upper limit of the content of the foamy cleaning composition is preferably 15% by mass or less, more preferably 10% by mass or less. When the content is 15% by mass or less, foaming and foam quality are improved more efficiently. Ranges with any combination of the above upper and lower limits are also available for use.

Examples of the base material include water, solvents, polyhydric alcohols, oily components, surfactants, pH adjusters, chelating agents, preservatives, fragrances, antioxidants, thickeners, sugars, moisturizers, beauty components, and other known additives. As specific examples of each component exemplified as the base material, those described above can be appropriately used.

The dosage form of the foamy cleaning composition is prepared into a foamy form during use. The method for preparing the foamy dosage form is not particularly limited, and examples thereof include a pump foamer, a squeeze foamer, and a shaking operation.

The use of the foamy cleaning composition is not particularly limited, and it can be applied to foamy cleansing agents, facial cleansers, body soaps, shampoos, and the like.

Deodorant Cosmetic

The deodorant cosmetic contains ethanol and menthol or a derivative thereof as active components in addition to the base material. Ethanol is blended for sterilization or deodorant improvement.

Application of the deodorant cosmetic as a nanobubble cosmetic containing ethanol and menthol or a derivative thereof as active components improves the deodorant derived from ethanol and menthol or a derivative thereof. This reduces the amount of ethanol and menthol or a derivative thereof used.

The lower limit of the content of ethanol in the deodorant cosmetic is preferably 30% by mass or more, more preferably 50% by mass or more. When the content is 30% by mass or more, the sterilization or deodorant is further improved. The upper limit of the content of ethanol is preferably 80% by mass or less, more preferably 75% by mass or less. When the content is 80% by mass or less, discomfort due to ethanol is reduced. Ranges with any combination of the above upper and lower limits are also available for use.

The lower limit of the content of menthol or a derivative thereof in the deodorant cosmetic is preferably 0.05% by mass or more, more preferably 0.1% by mass or more. When the content is 0.05% by mass or more, the refreshing feeling is further improved. The upper limit of the content of menthol or a derivative thereof is preferably 2% by mass or less, more preferably 1% by mass or less. When the content is 2% by mass or less, the refreshing feeling is improved more efficiently. In addition, discomfort due to menthol is reduced. Ranges with any combination of the above upper and lower limits are also available for use.

The dosage form of the deodorant cosmetic is not particularly limited, and examples thereof include liquid form, mist form, sheet form, and cream form.

Examples of the base material include water, alcohol other than ethanol, antiperspirants, cooling agents, antibacterial agents, anti-inflammatory agents, wetting agents such as polyhydric alcohols, surfactants, sweeteners, medicinal ingredients, pH adjusters, chelating agents, preservatives, fragrances, antioxidants, moisturizers, and other known additives.

Specific examples of the antiperspirant include zinc phenolsulfonate and aluminum chloride hydrate. These antiperspirants may be contained singly or in a combination of two or more.

Specific examples of the cooling agent include isopulegol and camphor. These cooling agents may be contained singly or in a combination of two or more.

As specific examples of the other components, those applicable as a deodorant cosmetic from among the specific examples described above can be appropriately used.

Perfuming Cosmetic

The perfuming cosmetic contains ethanol and polysorbate 20 as active components in addition to the base material including perfume and the like. Ethanol is used as a solvent and blended for sterilization or deodorant improvement. Polysorbate 20 emulsifies perfume components such as essential oils. Application of the perfuming cosmetic as a nanobubble cosmetic containing ethanol and polysorbate 20 as active components improves the persistence of the fragrance of the perfume components due to ethanol and polysorbate 20. This reduces the amount of ethanol used.

The lower limit of the content of ethanol in the perfuming cosmetic is preferably 5% by mass or more, more preferably 10% by mass or more. When the content is 5% by mass or more, the sterilization or deodorant is further improved. In addition, the solubility of the perfume component is improved. The upper limit of the content of ethanol is preferably 30% by mass or less, more preferably 20% by mass or less. When the content is 30% by mass or less, the solubility of the perfume component is improved more efficiently. Ranges with any combination of the above upper and lower limits are also available for use.

The lower limit of the content of polysorbate 20 in the perfuming cosmetic is preferably 0.5% by mass or more, more preferably 1% by mass or more. When the content is 0.5% by mass or more, the solubility of the perfume component is further improved. The upper limit of the content of polysorbate 20 is preferably 10% by mass or less, more preferably 5% by mass or less. When the content is 10% by mass or less, the solubility of the perfume component is improved more efficiently. Ranges with any combination of the above upper and lower limits are also available for use.

The dosage form of the perfuming cosmetic is not particularly limited, and examples thereof include liquid form, mist form, sheet form, and cream form.

Examples of the base material include water, alcohol other than ethanol, antiperspirants, cooling agents, antibacterial agents, anti-inflammatory agents, wetting agents such as polyhydric alcohols, surfactants, sweeteners, medicinal ingredients, pH adjusters, chelating agents, preservatives, fragrances, antioxidants, moisturizers, and other known additives.

As specific examples of the other components, those applicable as a perfuming cosmetic from among the specific examples described above can be appropriately used.

The effect of the topical composition for a nanobubble cosmetic according to the present embodiment will be described.

(1) The topical composition for a nanobubble cosmetic of the present embodiment contains, as an active ingredient, one of the following: polyoxypropylene diglyceryl ether and ethoxydiglycol; hyaluronic acid or a salt thereof; ethanol and menthol or a derivative thereof; sorbitol and glycerin; di(phytosteryl/octyldodecyl) lauroyl glutamate; glycereth-26; hydrogenated lecithin and polysorbate 20; or ethanol and polysorbate 20. The topical composition for a nanobubble cosmetic is used in a container equipped with a device mechanism for generating nanobubbles to further improve the functionality of cosmetics. In particular, this improves the penetrating properties and adhesion of specific active components to skin or hair, and further improves the function obtained by each active component. In addition, further improving the function obtained by each active component reduces the amount of the active component used while maintaining the functionality.

(2) When applied as the cleansing agent, the topical composition for a nanobubble cosmetic of the present embodiment contains polyoxypropylene diglyceryl ether and ethoxydiglycol as active components in addition to the base material. Application of the cleansing agent as a nanobubble cosmetic containing polyoxypropylene diglyceryl ether and ethoxydiglycol as active ingredients further improves the detergency and makeup removing effect. More specifically, the cleansing power, keratotic plug removal effect, pore cleaning effect, and the like are improved. As a result, it is possible to improve the touch feeling and refreshing feeling after washing. In addition, it is possible to improve washability and reduce stickiness during use.

(3) When applied as a beauty essence or lotion, the topical composition for a nanobubble cosmetic of the present embodiment contains hyaluronic acid or a salt thereof as an active component in addition to the base material. Application of the beauty essence or lotion as a nanobubble cosmetic containing hyaluronic acid or a salt thereof as an active component improves penetrating properties and improve feeling of use such as penetrating feel, refreshing feeling, and firmness. In addition, while suppressing stickiness, skin familiarity is made faster.

(4) When applied as a mouthwash, the topical composition for a nanobubble cosmetic of the present embodiment contains ethanol and menthol or a derivative thereof as an active component in addition to the base material. Application of the mouthwash as a nanobubble cosmetic containing ethanol and menthol or a derivative thereof as an active component improves the detergency of ethanol and the function of menthol. This improves the bad breath prevention effect and dental plaque removal effect while reducing alcohol-derived discomfort. In addition, the stickiness during use is reduced, and the sustainability of the refreshing feeling is improved.

(5) When applied as a facial cleansing composition, the topical composition for a nanobubble cosmetic of the present embodiment contains di(phytosteryl/octyldodecyl) lauroyl glutamate as an active component in addition to the base material. Application of the facial cleansing composition as a nanobubble cosmetic containing di(phytosteryl/octyldodecyl) lauroyl glutamate as an active component improves the moisturizing feeling after use in particular, and improve the feeling of use by suppressing the feeling of tightness after washing. In addition, the detergency during face washing is improved.

(6) When applied as an emulsion, the topical composition for a nanobubble cosmetic of the present embodiment contains hydrogenated lecithin and polysorbate 20 as active components in addition to the base material. Application of the emulsion as a nanobubble cosmetic containing hydrogenated lecithin and polysorbate 20 as active components improves the penetrating properties and improves the feeling of use such as penetrating feel.

(7) When applied as a foamy cleaning composition, the topical composition for a nanobubble cosmetic of the present embodiment contains sorbitol and glycerin as active components in addition to the base material. Application of the foamy cleaning composition as a nanobubble cosmetic containing sorbitol and glycerin as active components improves the foam quality.

(8) When applied as a deodorant cosmetic, the topical composition for a nanobubble cosmetic of the present embodiment contains ethanol and menthol or a derivative thereof as an active component in addition to the base material. Application of the deodorant cosmetic as a nanobubble cosmetic containing ethanol and menthol or a derivative thereof as active components improves the deodorant derived from ethanol and menthol or a derivative thereof. This reduces the amount of ethanol and menthol or a derivative thereof to be used while maintaining deodorant.

(9) When applied as a perfuming cosmetic, the topical composition for a nanobubble cosmetic of the present embodiment contains ethanol and polysorbate 20 as active components in addition to the base material. The perfuming cosmetic is applied as a nanobubble cosmetic containing ethanol and polysorbate 20 as active components improves the solubility of the perfume component due to ethanol and polysorbate 20 and improves of the persistence of the fragrance of the perfume component. This reduces the amount of ethanol used while maintaining the persistence of the fragrance.

(10) When applied as a lotion, the topical composition for a nanobubble cosmetic of the present embodiment contains glycereth-26 as an active component in addition to the base material. Application of the lotion as a nanobubble cosmetic containing glycereth-26 as an active component improves penetrating properties and improves feeling of use such as penetrating feel, refreshing feeling, and firmness.

The present embodiment described above can be performed with the following modifications. The present embodiment and the following modifications can be performed in a combination to the extent that they do not conflict technically.

A configuration other than the above may be adopted for the container equipped with a device mechanism for generating nanobubbles, the container filled with or holding the topical composition for a nanobubble cosmetic of the above embodiment.

The topical composition for a nanobubble cosmetic of the above embodiment may be used together with a container equipped with a device mechanism for generating nanobubbles, and the nanobubbles generated by the container equipped with a device mechanism for generating nanobubbles may be used by mixing with the topical composition for a nanobubble cosmetic.

EXAMPLES

Examples will be given below in order to describe the features and effects of the present invention more specifically, but the present invention is not limited to these examples.

Test Example 1: Cleansing Agent

Each cleansing agent containing the respective components shown in Table 1 was prepared. The numerical values in the column indicating each component in the table indicate the contents of the component in the column, and the unit is % by mass. The cleansing agent of each of Examples 1 and 2 and Comparative Examples 2 and 3 was used to fill the container equipped with a device mechanism for generating nanobubbles disclosed in Patent Document 1. The discharge type was a dispenser pump type, and the dosage form was liquid form. The cleansing agent of Comparative Example 1 was used to fill the same container as in Example 1, except that there was no device mechanism for generating nanobubbles. Each of the obtained cleansing agents was evaluated for detergency and makeup removing effect shown below.

Detergency

Ten panelists used the cleansing agent of each example in the usual manner. Specifically, about 0.5 g of each example was picked up and cleansing was performed. The number of panelists who determined that the detergency was excellent was counted. The results are shown in Table 1.

Makeup Removing

Ten panelists used the cleansing agent of each example in the usual manner for removing makeup. Specifically, about 0.5 g of each example was picked up and cleansing was performed. The number of panelists who determined that the makeup removing effect was excellent was counted. The results are shown in Table 1.

TABLE 1

| Component | Example 1 | Example 2 | Comparative Example 1 | Comparative Example 2 | Comparative Example 3 |
|---|---|---|---|---|---|
| PPG-9 diglyceryl ether | 10 | 15 | 10 | — | 10 |
| Ethoxydiglycol | 2 | 5 | 2 | 2 | — |
| Methyl gluceth-20 | — | — | — | 10 | — |
| Propylene glycol (PG) | — | — | — | — | 2 |
| Butylene glycol (BG) | 2 | 2 | 2 | 2 | 2 |
| Dipropylene glycol (DPG) | 3 | 3 | 3 | 3 | 3 |
| Pentylene glycol | 2 | 2 | 2 | 2 | 2 |
| Phenoxyethanol | 0.3 | 0.3 | 0.3 | 0.3 | 0.3 |
| Ethylhexylglycerin | 0.05 | 0.05 | 0.05 | 0.05 | 0.05 |
| Pentasodium pentetate | 0.008 | 0.008 | 0.008 | 0.008 | 0.008 |
| Citric acid | q.s. | q.s. | q.s. | q.s. | q.s. |
| Sodium citrate | q.s. | q.s. | q.s. | q.s. | q.s. |
| Purified water | Remainder | Remainder | Remainder | Remainder | Remainder |
| Total | 100 | 100 | 100 | 100 | 100 |
| Use of container equipped with nanobubble generation function | Used | Used | Not Used | Used | Used |
| Evaluation | | | | | |
| Detergency | 8 | 8 | 6 | 6 | 7 |
| Makeup removing | 8 | 9 | 6 | 6 | 7 |

Table 1 shows that there was an increase in the number of panelists who determined that the detergency and makeup removing effect were good when using the container equipped with a device mechanism for generating nanobubbles and containing the active component of the present invention.

Test Example 2: Beauty Essence

Each beauty essence containing the respective components shown in Table 2 was prepared. The numerical values in the column indicating each component in the table indicate the contents of the component in the column, and the unit is % by mass. The beauty essence of each of Examples 3 to 5 and Comparative Examples 5 to 7 was used to fill the container equipped with a device mechanism for generating nanobubbles disclosed in Patent Document 1. The discharge type was a dispenser pump type, and the dosage form was liquid form. The beauty essence of Comparative Example 4 was used fill the same container as in Example 3, except that there was no device mechanism for generating nanobubbles. Each of the obtained beauty essences was evaluated for penetrating power and stickiness shown below.

Penetrating Power

Ten panelists used the beauty essence of each example as a normal skin moisturizer. Specifically, about 0.3 g of each example was picked up and applied to their faces. The number of panelists who determined that the penetrating power (penetrating feel) was good was counted. The results are shown in Table 2.

Stickiness

The beauty essence was applied to their faces in the same manner as in the evaluation of penetrating power. The number of panelists who determined that the stickiness was low was counted. The results are shown in Table 2.

Comparative Example 9 was used to fill the container equipped with a device mechanism for generating nanobubbles disclosed in Patent Document 1. The discharge type was a dispenser pump type, and the dosage form was liquid form. The mouthwash of Comparative Example 8 was used to fill the same container as in Example 6, except that there was no device mechanism for generating nanobubbles. Each of the obtained mouthwashes was evaluated for detergency, low irritation, and refreshing feeling as described below.

Detergency

The mouths of 10 panelists were filled with about 20 mL of mouthwash of each example and washed for about 30

TABLE 2

| Component | Example 3 | Example 4 | Example 5 | Comparative Example 4 | Comparative Example 5 | Comparative Example 6 | Comparative Example 7 |
|---|---|---|---|---|---|---|---|
| Butylene glycol (BG) | 5 | 5 | 5 | 5 | 5 | 5 | 5 |
| Pentylene glycol | 2.3 | 2.3 | 2.3 | 2.3 | 2.3 | 2.3 | 2.3 |
| Sodium hyaluronate | 0.16 | 0.5 | 0.1 | 0.16 | — | — | — |
| CMC (cellulose gum) | — | — | — | — | 0.16 | — | — |
| Tamarind gum | — | — | — | — | — | 0.16 | — |
| Carrageenan | — | — | — | — | — | — | 0.16 |
| Pentasodium pentetate | 0.02 | 0.02 | 0.02 | 0.02 | 0.02 | 0.02 | 0.02 |
| Phenoxyethanol | 0.3 | 0.3 | 0.3 | 0.3 | 0.3 | 0.3 | 0.3 |
| Citric acid | q.s. | q.s. | q.s. | q.s. | q.s. | q.s. | q.s. |
| Sodium citrate | q.s. | q.s. | q.s. | q.s. | q.s. | q.s. | q.s. |
| Purified water | Remainder | Remainder | Remainder | Remainder | Remainder | Remainder | Remainder |
| Total | 100 | 100 | 100 | 100 | 100 | 100 | 100 |
| Use of container equipped with nanobubble generation function | With | With | With | Without | With | With | With |
| Evaluation |  |  |  |  |  |  |  |
| Penetrating power | 9 | 8 | 9 | 7 | 7 | 7 | 7 |
| Stickiness | 10 | 10 | 10 | 8 | 8 | 8 | 8 |

Table 2 shows that there was an increase in the number of panelists who determined that the penetrating power and stickiness-suppressing effect were good when using the container equipped with a device mechanism for generating nanobubbles and containing the active component.

Test Example 3: Mouthwash

Each mouthwash containing the respective components shown in Table 3 was prepared. The numerical values in the column indicating each component in the table indicate the contents of the component in the column, and the unit is % by mass. The mouthwash of each of Examples 6 to 8 and seconds. The number of panelists who determined that the detergency was good was counted. The results are shown in Table 3.

Low Irritation

Mouth washing was performed in the same manner as in the evaluation of detergency. The number of panelists who determined that the irritation was low was counted. The results are shown in Table 3.

Refreshing Feeling

Mouth washing was performed in the same manner as in the evaluation of detergency. The number of panelists who determined that the refreshing feeling was good was counted. The results are shown in Table 3.

TABLE 3

| Component | Example 6 | Example 7 | Example 8 | Comparative Example 8 | Comparative Example 9 |
|---|---|---|---|---|---|
| Glycerin | 8 | 8 | 8 | 8 | 8 |
| Sorbitol (70%) | 3 | 3 | 3 | 3 | 3 |
| Xylitol | 0.8 | 0.8 | 0.8 | 0.8 | 0.8 |
| Sodium hydrogen carbonate | 0.08 | 0.08 | 0.08 | 0.08 | 0.08 |
| Ethanol | 8 | 8 | 8 | 8 | 8 |
| l-Menthol | 0.07 | 0.01 | 0.15 | 0.07 | — |

TABLE 3-continued

| Component | Example 6 | Example 7 | Example 8 | Comparative Example 8 | Comparative Example 9 |
|---|---|---|---|---|---|
| Essential oil (citrus [lemon, grapefruit]) | — | — | — | — | 0.07 |
| PEG-60 hydrogenated castor oil | 0.7 | 0.7 | 0.7 | 0.7 | 0.7 |
| Flavor | q.s. | q.s. | q.s. | q.s. | q.s. |
| Preservative | q.s. | q.s. | q.s. | q.s. | q.s. |
| Purified water | Remainder | Remainder | Remainder | Remainder | Remainder |
| Total | 100 | 100 | 100 | 100 | 100 |
| Use of container equipped with nanobubble generation function | Used | Used | Used | Not Used | Used |
| Evaluation | | | | | |
| Detergency | 9 | 9 | 9 | 8 | 9 |
| Low irritation | 8 | 10 | 6 | 5 | 10 |
| Refreshing feeling | 10 | 8 | 10 | 9 | 5 |

Table 3 shows that there was an increase in the number of panelists who determined that the detergency, low irritation, and refreshing feeling were good when using the container equipped with a device mechanism for generating nanobubbles and containing the active component.

Test Example 4: Facial Cleansing Composition

Each facial cleansing composition containing the respective components shown in Table 4 was prepared. The numerical values in the column indicating each component in the table indicate the contents of the component in the column, and the unit is % by mass. The facial cleansing compositions of each of Example 9 and Comparative Example 11 was used to fill the container equipped with a device mechanism for generating nanobubbles disclosed in Patent Document 1. The discharge type was a dispenser pump type, and the dosage form was liquid form. The facial cleansing composition of Comparative Example 10 was used to fill the same container as in Example 9, except that there was no device mechanism for generating nanobubbles. Each of the obtained facial cleansing compositions was evaluated for the detergency shown below.

Detergency

Ten panelists used the facial cleansing composition of each example in the usual manner. Specifically, about 0.5 g of each example was picked up and face washing was performed. The number of panelists who determined that the detergency was excellent was counted. The results are shown in Table 4.

Feeling of Use

Face washing was performed in the same manner as in the above evaluation of detergency. The number of panelists who determined that there was little feeling of tightness after washing was counted. The results are shown in Table 4.

TABLE 4

| Component | Example 9 | Comparative Example 10 | Comparative Example 11 |
|---|---|---|---|
| Lauric acid | 12 | 12 | 12.05 |
| Myristic acid | 8 | 8 | 8 |
| Potassium hydroxide | 6.75 | 6.75 | 6.75 |
| Butylene glycol (BG) | 6 | 6 | 6 |
| Palmitic acid | 5 | 5 | 5 |
| Glycerin | 5 | 5 | 5 |
| Glycol distearate | 3 | 3 | 3 |
| Cocoylglycine K | 1.2 | 1.2 | 1.2 |

TABLE 4-continued

| Component | Example 9 | Comparative Example 10 | Comparative Example 11 |
|---|---|---|---|
| Hydroxypropyl methylcellulose | 0.4 | 0.4 | 0.4 |
| Pentasodium pentetate | 0.08 | 0.08 | 0.08 |
| Di(phytosteryl/octyldodecyl) lauroyl glutamate | 0.05 | 0.05 | — |
| Purified water | Remainder | Remainder | Remainder |
| Total | 100 | 100 | 100 |
| Use of container equipped with nanobubble generation function | Used | Not Used | Used |
| Evaluation | | | |
| Detergency | 9 | 6 | 7 |
| Feeling of Use | 8 | 5 | 7 |

Table 4 shows that there was an increase in the number of panelists who determined that the detergency and feeling of use were good when using the container equipped with a device mechanism for generating nanobubbles and containing the active component.

Test Example 5: Emulsion

Each emulsion containing the respective components shown in Table 5 was prepared. The numerical values in the column indicating each component in the table indicate the contents of the component in the column, and the unit is % by mass. The emulsion of each of Example 10 and Comparative Example 13 was used to fill the container equipped with a device mechanism for generating nanobubbles disclosed in Patent Document 1. The discharge type was a dispenser pump type, and the dosage form was liquid form. The emulsion of Comparative Example 12 was used to fill the same container as in Example 10, except that there was no device mechanism for generating nanobubbles. Each of the obtained emulsions was evaluated for penetrating power shown below.

Penetrating Power

Ten panelists used the emulsion of each example as a normal skin moisturizer. Specifically, about 0.3 g of each example was picked up and applied to their faces. The number of panelists who determined that the penetrating power (penetrating feel) was good was counted. The results are shown in Table 5.

TABLE 5

| Component | Example 10 | Comparative Example 12 | Comparative Example 13 |
|---|---|---|---|
| Butylene glycol (BG) | 6.2 | 6.2 | 6.2 |
| Squalane | 6 | 6 | 6 |
| Pentylene glycol | 2.5 | 2.5 | 2.5 |
| Glycerin | 1.6 | 1.6 | 1.6 |
| Diglycerin | 1.4 | 1.4 | 1.4 |
| Hydrogenated lecithin | 1 | 1 | 1.15 |
| Sucrose | 1 | 1 | 1 |
| PEG/PPG/polybutylene glycol-8/5/3 glycerin | 1 | 1 | 1 |
| Maltitol | 0.75 | 0.75 | 0.75 |
| Phenoxyethanol | 0.3 | 0.3 | 0.3 |
| 1,2-Hexanediol | 0.2 | 0.2 | 0.2 |
| Polysorbate 20 | 0.15 | 0.15 | — |
| Ethylhexylglycerin | 0.05 | 0.05 | 0.05 |
| Pentasodium pentetate | 0.02 | 0.02 | 0.02 |
| Potassium hydroxide | q.s. | q.s. | q.s. |
| (Acrylates/C10-30 alkyl acrylate) crosspolymer | q.s. | q.s. | q.s. |
| Xanthan gum | q.s. | q.s. | q.s. |
| Purified water | Remainder | Remainder | Remainder |
| Total | 100 | 100 | 100 |
| Use of container equipped with nanobubble generation function | Used | Not Used | Used |
| Evaluation | | | |
| Penetrating power | 10 | 7 | 8 |

Table 5 shows that there was an increase in the number of panelists who determined that the penetrating power was good when using the container equipped with a device mechanism for generating nanobubbles and containing the active component.

Test Example 6: Foamy Cleaning Composition

Each foamy cleaning composition containing the respective components shown in Table 6 was prepared. The numerical values in the column indicating each component in the table indicate the contents of the component in the column, and the unit is % by mass. The foamy cleaning composition of each of Example 11 and Comparative Examples 15 and 16 was used to fill the container equipped with a device mechanism for generating nanobubbles disclosed in Patent Document 1. The discharge type was a pump foamer discharge type, and the dosage form was foam. The foamy cleaning composition of Comparative Example 14 was used to fill the same container as in Example 11, except that there was no device mechanism for generating nanobubbles. Each of the obtained foamy cleaning compositions was evaluated for the foam quality shown below.

Foam Quality

Ten panelists picked up the foamy cleaning composition of each example and checked the touch feel of the foam. The number of panelists who determined that the foam quality was excellent was counted. The results are shown in Table 6.

TABLE 6

| Component | Example 11 | Comparative Example 14 | Comparative Example 15 | Comparative Example 16 |
|---|---|---|---|---|
| Butylene glycol (BG) | 11 | 11 | 16 | 13.1 |
| Cocoyl glutamic acid triethanolamine | 10.5 | 10.5 | 10.5 | 10.5 |
| Cocamide diethanolamine | 5 | 5 | 5 | 5 |
| Diglycerin | 5 | 5 | 5 | 5 |
| Glycerin | 5 | 5 | — | 5 |
| Sorbitol | 2.1 | 2.1 | 2.1 | — |
| Lauryl hydroxy sultaine | 1.5 | 1.5 | 1.5 | 1.5 |
| Decyl glucoside | 0.424 | 0.424 | 0.424 | 0.424 |
| Ethylhexylglycerin | 0.05 | 0.05 | 0.05 | 0.05 |
| Pentasodium pentetate | 0.02 | 0.02 | 0.02 | 0.02 |
| Purified water | Remainder | Remainder | Remainder | Remainder |
| Total | 100 | 100 | 100 | 100 |
| Container equipped with nanobubble generation function | Used | Not Used | Used | Used |
| Evaluation | | | | |
| Foam quality | 9 | 6 | 7 | 7 |

Table 6 shows that there was an increase in the number of panelists who determined that the foam quality was good when using the container equipped with a device mechanism for generating nanobubbles and containing the active component.

Test Example 7: Deodorant Cosmetic

Each deodorant cosmetic containing the respective components shown in Table 7 was prepared. The numerical values in the column indicating each component in the table indicate the contents of the component in the column, and the unit is % by mass. The deodorant cosmetic of each of Examples 12 and 13 was used to fill the container equipped with a device mechanism for generating nanobubbles disclosed in Patent Document 1. The discharge type was a mist pump type, and the dosage form was mist. The deodorant cosmetic of Comparative Example 17 was used to fill the same container as in Example 12, except that there was no device mechanism for generating nanobubbles. Each of the obtained deodorant cosmetics was evaluated for the deodorant effect shown below.

Deodorant Effect

Ten panelists sprayed the deodorant cosmetic of each example onto used underwear to check the deodorant effect. The number of panelists who determined that the deodorant effect was excellent was counted. The results are shown in Table 7.

TABLE 7

| Component | Example 12 | Example 13 | Comparative Example 17 |
|---|---|---|---|
| Ethanol | 69.4 | 69.4 | 69.4 |
| Isopulegol | 3 | 3 | 3 |
| Zinc phenolsulfonate | 2 | 2 | 2 |
| Menthol | 0.4 | 0.2 | 0.4 |

TABLE 7-continued

| Component | Example 12 | Example 13 | Comparative Example 17 |
|---|---|---|---|
| Camphor | 0.1 | 0.1 | 0.1 |
| o-Cymen-5-ol | 0.1 | 0.1 | 0.1 |
| Purified water | Remainder | Remainder | Remainder |
| Total | 100 | 100 | 100 |
| Use of container equipped with nanobubble generation function | Used | Used | Not Used |
| Evaluation | | | |
| Deodorant effect | 10 | 8 | 7 |

Table 7 shows that there was an increase in the number of panelists who determined that the deodorant effect was good when using the container equipped with a device mechanism for generating nanobubbles and containing the active component. The amount of menthol used was able to be reduced while maintaining deodorant.

Test Example 8: Perfuming Cosmetic

Each perfuming cosmetic containing the respective components shown in Table 8 was prepared. The numerical values in the column indicating each component in the table indicate the contents of the component in the column, and the unit is % by mass. The perfuming cosmetic of each of Examples 14 and 15 was used to fill the container equipped with a device mechanism for generating nanobubbles disclosed in Patent Document 1. The discharge type was a mist pump type, and the dosage form was mist. The perfuming cosmetic of Comparative Example 18 was used to fill the same container as in Example 14, except that there was no device mechanism for generating nanobubbles. Each of the obtained perfuming cosmetics was evaluated for the fragrance persistence shown below.

Fragrance Persistence

Ten panelists sprayed the perfuming cosmetic of each example onto their wrists, and the fragrance was checked immediately after the spraying and after the elapse of a predetermined time to evaluate fragrance persistence. The number of panelists who determined that the fragrance persistence was excellent was counted. The results are shown in Table 8.

TABLE 8

| Component | Example 14 | Example 15 | Comparative Example 18 |
|---|---|---|---|
| Ethanol | 15 | 10 | 15 |
| Dipropylene glycol | 5 | 5 | 5 |
| Polysorbate 20 | 4 | 4 | 4 |
| Butylene glycol (BG) | 3 | 3 | 3 |
| Glycerin | 1 | 1 | 1 |
| Phenoxyethanol | 0.1 | 0.1 | 0.1 |
| Flavor | q.s. | q.s. | q.s. |
| Sodium citrate | q.s. | q.s. | q.s. |
| Citric acid | q.s. | q.s. | q.s. |
| Purified water | Remainder | Remainder | Remainder |
| Total | 100 | 100 | 100 |
| Use of container equipped with nanobubble generation function | Used | Used | Not Used |
| Evaluation | | | |
| Fragrance persistence | 10 | 8 | 7 |

Table 8 shows that there was an increase in the number of panelists who determined that the fragrance persistence was good when using the container equipped with a device mechanism for generating nanobubbles and containing the active component. The amount of ethanol used, which is a solvent for flavors, can be reduced, and discomfort during use can be reduced.

Test Example 9: Lotion

Each lotion containing the respective components shown in Table 9 was prepared. The numerical values in the column indicating each component in the table indicate the contents of the component in the column, and the unit is % by mass. The lotion of Example 16 was used to fill the container equipped with a device mechanism for generating nanobubbles disclosed in Patent Document 1. The discharge type was a dispenser pump type, and the dosage form was liquid form. The lotion of Comparative Example 19 was used to fill the same container as in Example 16, except that there was no device mechanism for generating nanobubbles. Each of the obtained beauty essences was evaluated for penetrating power shown below.

Penetrating Power

Ten panelists used the lotion of each example as a normal skin moisturizer. Specifically, about 0.3 g of each example was picked up and applied to their faces. The number of panelists who determined that the penetrating power (penetrating feel) was good was counted. The results are shown in Table 9.

TABLE 9

| Component (lotion) | Example 16 | Comparative Example 19 |
|---|---|---|
| Glycerin | 5 | 5 |
| Butylene glycol (BG) | 5 | 5 |
| Pentylene glycol | 3 | 3 |
| PEG-32 | 2.5 | 2.5 |
| Xylitol | 1 | 1 |
| Glycereth-26 | 1 | 1 |
| Betaine | 0.5 | 0.5 |
| PPG-6 decyltetradeceth-20 | 0.35 | 0.35 |
| Phenoxyethanol | 0.35 | 0.35 |
| Ethylhexylglycerin | 0.05 | 0.05 |
| Lauryl Betaine | 0.03 | 0.03 |
| Pentasodium pentetate | 0.02 | 0.02 |
| Sodium hyaluronate | 0.015 | 0.015 |
| Xanthan gum | q.s. | q.s. |
| Carbomer | q.s. | q.s. |
| Potassium hydroxide | q.s. | q.s. |
| Purified water | Remainder | Remainder |
| Total | 100 | 100 |
| Use of container equipped with nanobubble generation function | Used | Not Used |
| Evaluation | | |
| Penetrating power | 9 | 6 |

Table 9 shows that there was an increase in the number of panelists who determined that the penetrating power was good when using the container equipped with a device mechanism for generating nanobubbles and containing the active component.

The technical ideas obtainable from the above embodiments and the modifications are described below.

(a) A topical composition for a nanobubble cosmetic, the topical composition being used as a cleansing agent, beauty essence, facial cleanser, lotion, emulsion, pack cosmetic, body soap, body care, deodorant cosmetic, perfuming cosmetic, anti-wrinkle cosmetic, acne care cosmetic, hand care cosmetic, sunscreen, foundation, nail polish, nail polish remover, acne care agent, hand sanitizer, shampoo, rinse, treatment, conditioner, hair restorer, hair dye, bleaching agents, hair styling agents, mouthwash, or mouth spray.

The invention claimed is:

1. A method for preparing a cleansing agent as a nanobubble cosmetic, the method comprising the steps of:
filling, with a topical composition, a container equipped with a device mechanism for generating nanobubbles, wherein the device mechanism includes:
a piston;
a piston guide;
a discharge port; and
a gap provided in the middle of a passage that communicates with the discharge port, arranged between the piston and the piston guide, wherein the topical composition passes through the gap between the piston and the piston guide and is discharged from the discharge port, wherein the gap provided in the middle of the passage that communicates with the discharge port causes the topical composition to undergo a shear crushing action to generate nanobubbles, and wherein the topical composition contains polyoxypropylene diglyceryl ether and ethoxydiglycol; and
generating nanobubbles in the topical composition with the device mechanism.

* * * * *